United States Patent [19]

Chabardes et al.

[11] Patent Number: 5,250,710
[45] Date of Patent: Oct. 5, 1993

[54] DIHYDROPYRAN DERIVATIVES, PROCESSES FOR PREPARATION AND USE

[75] Inventors: Pierre F. Chabardes, Sainte Foy Les Lyon; Lucette Duhamel; Pierre Duhamel, both of Mont Saint Aignan; Jerome Guillemont, Beuzeville; Jean-Marie Poirier, Saint Martin de Vivier, all of France

[73] Assignee: Rhone-Poulenc Nutrition Animale, Commentry, France

[21] Appl. No.: 879,335

[22] Filed: May 7, 1992

Related U.S. Application Data

[62] Division of Ser. No. 620,609, Dec. 3, 1990, Pat. No. 5,157,133.

[30] Foreign Application Priority Data

Dec. 1, 1989 [FR] France ................. 89 15869

[51] Int. Cl.$^5$ ............................ C07D 315/00
[52] U.S. Cl. .................. 549/423; 568/447; 568/463; 568/496
[58] Field of Search ........................ 549/423

[56] References Cited

U.S. PATENT DOCUMENTS 3,159,653 12/1964 Falbe et al. .................. 549/423
3,655,695 4/1972 Andrews .................. 549/423

OTHER PUBLICATIONS

Carey, Francis *Organic Chemistry* McGraw Hill Book Co., N.Y., p. 560 (1987).

*Primary Examiner*—Glennon H. Hollrah
*Assistant Examiner*—Brian M. Burn
*Attorney, Agent, or Firm*—Finnegan, Henderson, Farabow, Garrett & Dunner

[57] ABSTRACT

The present invention relates to dihydropyran derivatives, processes for preparing, and processes of using the derivatives. The derivatives are prepared by condensation of lithium dienolate of prenal with an aldehyde or a ketone.

The pyran derivative prepared from β-ionylideneacetaldehyde when treated in the presence of a catalyst directly forms retinal.

3 Claims, No Drawings

DIHYDROPYRAN DERIVATIVES, PROCESSES FOR PREPARATION AND USE

This is a division of application Ser. No. 07/620,609, filed Dec. 3, 1990, now U.S. Pat. No. 5,157,133.

This application is related to French Patent Application No. 8915869, filed on Dec. 1, 1989, the disclosure of which is entirely incorporated by reference herein.

BACKGROUND OF THE INVENTION

1. Field of the Invention

The present invention relates to dihydropyran derivatives, to processes for preparing these derivatives and to processes for preparing vitamin intermediates, in particular vitamins A and E intermediates, using the dihydropyran derivatives.

2. Description of the Art

According to Japanese Patents J53-101308 and J53-101309, vitamin A intermediates may be prepared by the hydrolysis of dihydropyran derivatives bearing an alkyl radical at the 4-position and optionally a hydroxyl group at the 2-position. The process for preparing these derivatives is carried out by the hydrogenation of a hydroperoxide on a palladium- or platinum-based catalyst. However, dihydropyran derivatives substituted at the 6-position with a polyene chain can not be obtained with the prior art process.

SUMMARY OF THE INVENTION

The present invention relates to novel dihydropyran derivatives which are substituted at the 6-position with various radicals. The dihydropyran derivatives are of formula I:

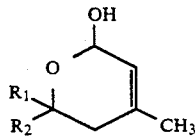

wherein $R_1$ and $R_2$, which may be identical or different, are hydrogen, linear or branched alkyl groups, linear or branched alkenyl groups, or aryl groups, but are not simultaneously hydrogen.

The present invention also relates to a process for preparing dihydropyran derivatives which are substituted at the 6-position. The process comprises contacting lithium dienolate of prenal with an aldehyde or a ketone.

Further, the present invention relates to the preparation of vitamin intermediates by the hydrolysis of dihydropyrans.

DESCRIPTION OF THE PREFERRED EMBODIMENTS

Novel dihydropyran derivatives of the present invention are of formula:

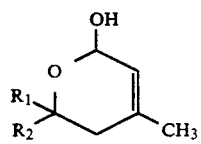

wherein $R_1$ and $R_2$, which may be identical or different, are hydrogen, linear or branched alkyl groups, linear or branched alkenyl groups, or aryl groups, but are not simultaneously hydrogen.

The alkyl groups, alkenyl groups, and aryl groups preferably have 1 to 18 carbon atoms. Most preferred are derivatives of formula I wherein $R_2$ is hydrogen and $R_1$ is 6-[2-methyl-4-(2,6,6-trimethyl-1-cyclohexenyl)-butadienyl] of formula Ia:

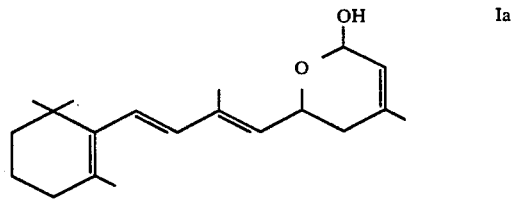

Compounds of formula I are prepared according to a process of condensation comprising contacting lithium dienolate of prenal of formula:

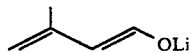

with an aldehyde of formula $R_1CHO$ or a ketone of formula $R_1—CO—R_2$, the radicals $R_1$ and $R_2$ are as defined above. Preferred materials are β-ionylideneacetaldehyde and lithium dienolate of prenal.

The condensation preferably takes place in the presence of a solvent which is inert under the reaction conditions. The solvent may be selected from ethers such as tetrahydrofuran and aliphatic or aromatic hydrocarbons such as pentane, hexane, toluene and xylenes. The condensation preferably takes place at a temperature of between $-80°$ C. and $+20°$ C.

The preparation of lithium dienolate of prenal may be carried out by at least two methods. A first method comprises contacting (a) a (3-methylbutadienyloxy)silane of formula II:

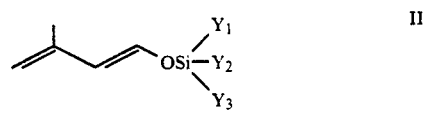

wherein $Y_1$, $Y_2$ and $Y_3$, which may be identical or different, are alkyl groups containing 1 to 4 carbon atoms, preferably a methyl group, or aryl groups containing 6 to 12 carbon atoms, preferably a phenyl group, with (b) a lithium derivative of formula R'Li, wherein R' is a linear or branched alkyl group containing 1 to 4 carbon atoms, preferably a methyl or tert-butyl group.

The reactants are preferably contacted at a temperature of between $-80°$ C. and $0°$ C., either in the absence of solvent or in a solvent which is inert under the reaction conditions. The solvents may be selected from ethers such as tetrahydrofuran, and aliphatic or aromatic hydrocarbons such as pentane, hexane, toluene and xylenes.

The mole ratio of the lithium derivative R'Li to the compound of formula II is preferably greater than 1, and most preferably between 1 and 1.2.

A second method for the preparation of lithium dienolate of prenal comprises contacting (a) an ester of 3-methylbutadienol of formula III:

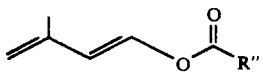

wherein R" is a linear or branched alkyl group, preferably containing 1 to 6 carbon atoms, or an aryl group, preferably containing 6 to 12 carbon atoms, with (b) a lithium derivative of formula R'Li, wherein R' is a linear or branched alkyl group containing 1 to 4 carbon atoms, preferably a methyl or tert-butyl group.

Preferably R" represents a methyl group, and formula III represents 1-acetoxy-3-methyl-butadiene.

The compound of formula III and the lithium derivative are preferably contacted at a temperature of between −80° C. and 0° C., either in the absence of solvent or in a solvent which is inert under the reaction conditions. The solvents may be selected from ethers, preferably tetrahydrofuran, and aliphatic or aromatic hydrocarbons such as pentane, hexane, toluene and xylenes.

The mole ratio of the lithium derivative R'Li to the compound of formula III is preferably greater than 2, and most preferably between 2 and 2.2.

The present invention also relates to the use of the compounds of formula I for the preparation of terpene intermediates, and preferably for the preparation of retinal.

The compounds of formula I are readily hydrolyzed to terpene aldehydes by the action of an acid in a solvent which is inert under the conditions of the reaction. Such solvents may be selected from ethers such as tetrahydrofuran, polar aprotic solvents such as dimethylformamide and N-methylpyrrolidone, and aliphatic or aromatic hydrocarbons such as pentane, hexane, toluene and xylenes. Preferably the solvent is a mixture of dimethylformamide and toluene.

The reaction may be illustrated diagrammatically in the following manner:

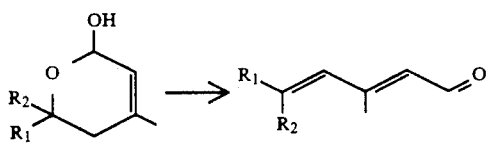

It is preferable to add an acid which permits catalysis of the reaction. These acids are preferably selected from trichloroacetic acid, trifluoroacetic acid, trifluoromethanesulphonic acid, pyridinium chloride, and boric acid. The most preferred acid is boric acid.

A catalytic amount of acid is used, preferably between 0.01 and 0.05 mole per mole of derivative of formula I to be hydrolyzed, and most preferably, 0.02 mole per mole of the derivative.

The sequence of reactions, namely formation of the lithium derivative, bringing into contact with the ketone or aldehyde, and hydrolysis of the pyran ring, can be performed without isolating the intermediate products ("one pot synthesis").

The following examples illustrate the present invention. However, these examples are illustrative and are not meant to limit the present invention.

EXAMPLE I

Preparation of the silyl enol ethers

Chlorotrimethylsilane (0.125 mol; 13.6 g) and triethylamine (0.125 mol; 12.6 g) were added to a solution of sodium iodide (0.125 mol; 18.7 g) in acetonitrile (130 ml). The mixture was cooled to a temperature below 10° C. and aldehyde (0.1 mol) was added dropwise. Stirring was continued for 3 to 12 hours at room temperature. The suspension was filtered and the product was extracted with pentane (5×40 ml). The pentane phase was evaporated and the residue then distilled. The product 3-Methyl-1-trimethylsiloxybutadiene

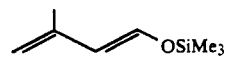

had a boiling point of 48°-50° C./18 mm Hg, and was recovered in a 75% yield.

EXAMPLE 2

Preparation of 1-acetoxy-3-methyl-1,3-butadiene

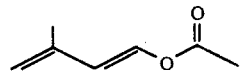

Prenal (0.332 mol) was run gradually into isopropenyl acetate (0.532 mol) in which paratoluenesulphonic acid (1% by weight) had been dissolved. The acetone was distilled off as it was formed. The temperature of the mixture was 93°-94° C. at the beginning and 118° C. after heating for 1 hour 50 minutes. The 1-acetoxy-3-methylbutadiene was then purified by distillation. The boiling point of the product was 48°-52° C./13 mm Hg.

EXAMPLE 3

CONDENSATION WITH CARBONYL DERIVATIVES (Table 1)

1) Use of 3-methyl-1-trimethylsiloxybutadiene a) With benzaldehyde: 6-Phenyl-4-methyl-2-hydroxy-2,5-dihydro-2H-pyran

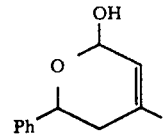

2.5N methyllithium (10 mmol; 4 ml) was added at −20° C. in the course of 5 minutes to a solution of silyl dienol ether (10 mmol; 1.56 g) in anhydrous tetrahydrofuran (THF) (15 ml). The reaction was exothermic and the solution became orange-yellow in color.

After 15 minutes at −20° C., the reaction medium was cooled to −70° C. and benzaldehyde (10 mmol) (experiment 3, Table 1) in THF (2 ml) was introduced. The mixture was left for 15 minutes at −70° C. The temperature of the reaction medium was raised gradually to −20° C. in the course of 90 minutes. The solution was then treated at −20° C. with saturated aqueous sodium hydrogen carbonate solution (15 ml). The product was extracted with ether (4×15 ml). Then the organic phase was dried over magnesium sulphate and filtered and the solvents were evaporated off. The crude reaction product was purified by flash chromatography. The eluent was ether/petroleum ether with a ratio of 20:100. The yield was 83% and the melting point was 90° C. The IR spectrum was 3600-3200 (ν OH) and 1600 (ν C═C).

b) With acetaldehyde: 4,6-Dimethyl-2-hydroxy-2,5-dihydro-2H-pyran

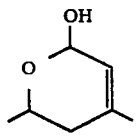

The eluent was ether/petroleum ether with a ratio of 20:100. The yield was 74% and the IR spectrum was 3600-3200 (ν OH) and 1640 (ν C═C).

c) With dehydrocitral: 6-(2,6-Dimethylheptatrienyl)-4-methyl-2-hyrodroxy-2,5-dihydro-2H-pyran

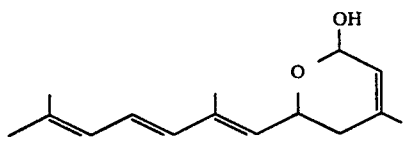

The eluent was ether/petroleum ether with a ratio of 20:100. The yield was 64.5% and the IR spectrum was 3600-3200 (ν OH) and 1670 (ν C═C).

d) With hexadienal: 6-(1,3-Pentadienyl)-4-methyl-2-hydroxy-2,5-dihydro-2H-pyran

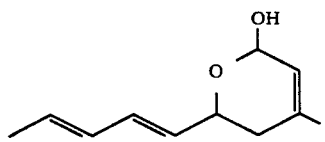

The eluent was ether/petroleum ether with a ratio of 20:100. The yield was 45% and the IR spectrum was 3600-3200 (ν OH) and 1670 (ν C═C).

e) With β-ionylideneacetaldehyde: 6-[2-Methyl-4-(2,6,6-trimethyl-1-cyclohexenyl)butadienyl]-4-methyl-2-hydroxy-2,5-dihydro-2H-pyran

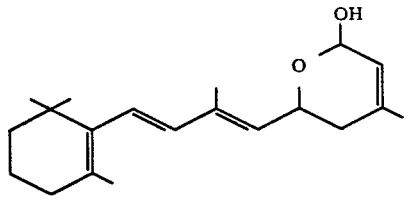

2.5N n-butyllithium (2.4 mmol; 0.96 ml) or 2.5N methyllithium (2.4 mmol; 0.96 ml) was added dropwise under argon at −20° C. to a solution of 3-methyl-1-trimethylsiloxybutadiene (2.4 mmol; 0.38 g) diluted in anhydrous tetrahydrofuran (5 ml). After contact for half an hour at −20° C., the solution, which had become yellow, was cooled to −45° C. β-Ionylideneacetaldehyde (2 mmol; 0.436 g), dissolved in anhydrous THF (2 ml), was introduced in the course of 5 minutes at −45° C. The mixture was left stirring for 3 hours at this temperature. The degree of progress of the reaction was monitored by TLC.

The reaction medium was treated at −45° C. with saturated aqueous sodium hydrogen carbonate solution (7 ml). The product was extracted with ether (4×10 ml) and the ether phase was dried over magnesium sulphate for one hour. After filtration, the solvents were evaporated off.

The crude product was purified by flash chromatography. A column 5 mm in diameter and silica (approximately 20 g for 0.5 g of crude product) were used. Unreacted β-ionylideneacetaldehyde (25%) and then the "C₂₀" pyran derivative were isolated successively. The eluent was ether/petroleum ether at a ratio of 20:100. The yield was 66% and the IR spectrum was 3600-3200: (ν OH) and 1650 (ν C═C).

2) Use of 1-acetoxy-3-methylbutadiene a) With isovaleraldehyde: 6-Isobutyl-4-methyl-2-hydroxy-2,5-dihydro-2H-pyran

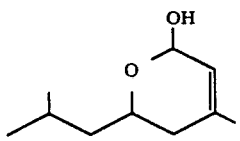

1.6N methyllithium (20 mmol; 12.5 ml) was added at −30° C. in the course of 5 minutes to a solution of 3-methyl-1-acetoxybutadiene (10 mmol) in anhydrous THF (15 ml). After 15 minutes at −30° C., the reaction medium was cooled to −70° C. and isovaleraldehyde (8.5 mmol) in THF (2 ml) was introduced. The temperature was raised to 20° C. in the course of one hour. The reaction medium was treated at −40° C. with saturated aqueous sodium hydrogen carbonate solution (15 ml). The product was extracted with ether (4×15 ml), the organic phase was dried over magnesium sulphate and filtered and the solvents were evaporated off. The crude reaction product was purified by flash chromatography. The eluent was ether/petroleum ether with a ratio of 20:100. The yield was 74% and the IR spectrum was 3600-3200 (ν OH) and 1650 (ν C═C).

b) With acetone: 4,6,6-Trimethyl-2-hydroxy-2,5-dihydro-2H-pyran

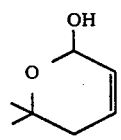

The eluent was ether/petroleum ether with a ratio of 20:100. The yield was 25% and the IR spectrum was 3600-3200 (ν OH) and 1650 (ν C═C).

The collective results are shown in Table 1.

EXAMPLE 4

Conversion of the pyran derivatives to polyene aldehydes (Tables 2 and 3)

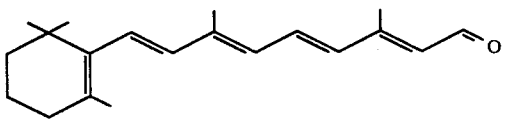

The pyran derivative (1 mmol; 0.3 g), was diluted in a mixture of dimethylformamide (DMF) (1.2 ml) and toluene (4.8 ml), and then boric acid (0.09 mmol; 5.6 ml), dissolved in DMF (1 ml) (see Table 2, experiment 4), were introduced under an inert atmosphere into a 25-ml two-necked flask equipped with a thermometer and a condenser.

The reaction mixture was placed in an oil bath heated beforehand to 110° C. After 15 minutes at this temperature, the spot of the "C20" pyran derivative had completely disappeared in TLC. The solution was then cooled to room temperature and was thereafter neutralized with saturated aqueous sodium hydrogen carbonate solution (5 ml). The aqueous phase was extracted with ether (4*10 ml), the ether phase was then dried over magnesium sulphate, and the solvents were concentrated in the presence of ionol. The product was purified by flash chromatography on silica. The eluent was ether/petroleum ether with a ratio of 5:100. The retinal was isolated in a 60% yield. The IR spectrum was 1665 (m C=O) and 1580 (m C=C).

Under the same conditions, using pyridinium chloride (0.09; mmol 10 mg), retinal was obtained in a 65% yield (Table 2, experiment 3).

The various results for the preparation of retinal are shown in Table 2.

The various polyene aldehydes prepared by the hydrolysis of pyran derivatives of formula (I), using pyridinium chloride as a catalyst under the conditions of experiment 3, Table 2, are shown in Table 3.

TABLE 1

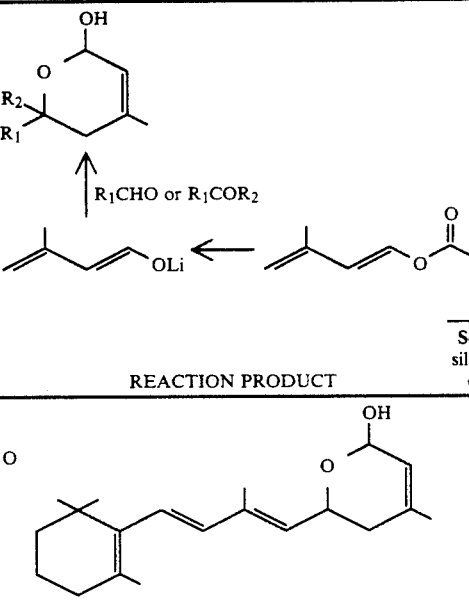

| EXPERI-MENT | R₁CHO or R₁COR₂ | REACTION PRODUCT | YIELD Source: silyl enol ether | YIELD Source: enol acetate |
| --- | --- | --- | --- | --- |
| 1 |  | 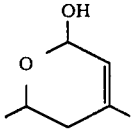 | 66 | 60 |
| 2 |  | 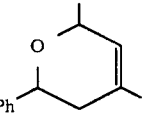 | 74 | |
| 3 | 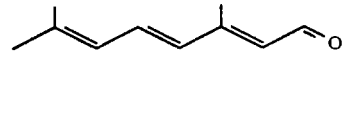 | 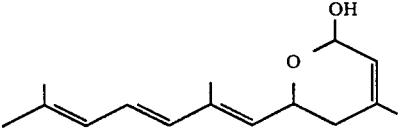 | 83 | 94 |
| 4 | 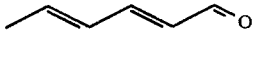 | 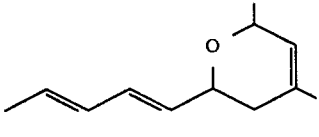 | 75.5 | |
| 5 | 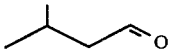 | 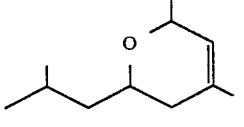 | 45 | 50 |
| 6 | | | 74 | |

TABLE 1-continued

| EXPERIMENT | R₁CHO or R₁COR₂ | REACTION PRODUCT | YIELD Source: silyl enol ether | YIELD Source: enol acetate |
|---|---|---|---|---|
| 7 | 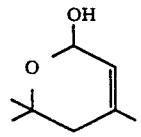 | 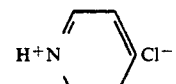 | | 25 |

TABLE 2

Preparation of retinal

| EXPERIMENT | CATALYST | mol % | T °C. | TIME (h) | YIELD % RETINAL |
|---|---|---|---|---|---|
| 1 | CCl₃CO₂H | 2 | 80 | 0.25 | 25 |
| 2 | CF₃CO₂H | 2 | R.T. | 18 | 45 |
| 3 | 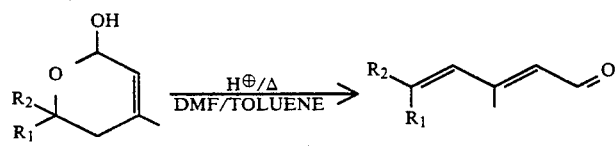 | 1 | 110 | 0.25 | 65 |

TABLE 2-continued

Preparation of retinal

| EXPERIMENT | CATALYST | mol % | T °C. | TIME (h) | YIELD % RETINAL |
|---|---|---|---|---|---|
| 4 | H₃BO₃ | 1 | 110 | 0.25 | 60 |

The yield is expressed in terms of the product purified by flash chromatography.

TABLE 3

PREPARATION OF THE POLYETHYLENIC ALDEHYDES

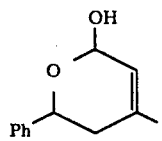

| Experiment | Pyran Derivative | Aldehyde | Yld % |
|---|---|---|---|
| 1 | 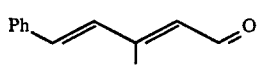 | 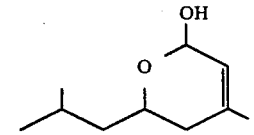 | 70 |
| 2 | 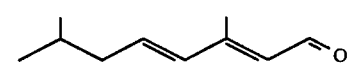 | 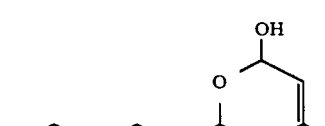 | 63 |
| 3 |  | | 69 |

TABLE 3-continued
PREPARATION OF THE POLYETHYLENIC ALDEHYDES

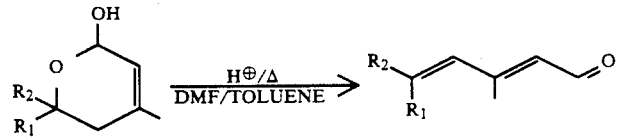

| Experiment | Pyran Derivative | Aldehyde | Yld % |
|---|---|---|---|
| 4 | 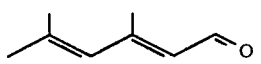 |  | 30 |
| 5 | 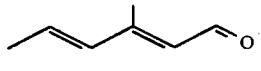 | 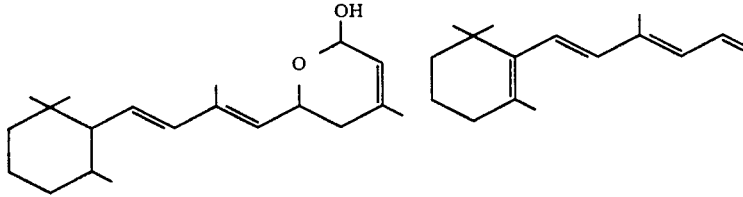 | 55 |
| 6 | 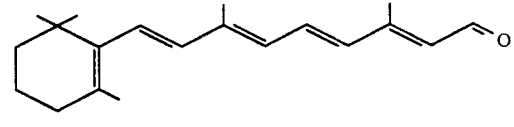 | 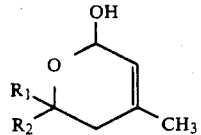 | 65 |

Catalyst: pyridinium chloride

What is claimed is:

1. A process for preparing dihydropyran derivatives of formula I:

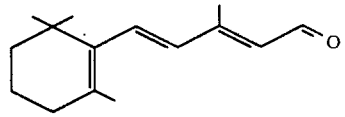

wherein $R_1$ and $R_2$, which may be identical or different, are hydrogen, linear or branched alkyl groups, linear or branched alkenyl groups or aryl groups, but are not simultaneously hydrogen, comprising contacting lithium dienolate of prenal with an aldehyde of formula $R_1CHO$ or a ketone of formula $R_1COR_2$, wherein $R_1$ and $R_2$ are defined as above.

2. The process for preparing derivatives according to claim 1, wherein the alkyl groups, alkenyl groups or aryl groups contain 1 to 18 carbon atoms.

3. The process for preparing derivatives according to claim 1, wherein the lithium dienolate of prenal is contacted with an aldehyde of formula $R_1CHO$, wherein the aldehyde is β-ionylideneacetaldehyde of formula:

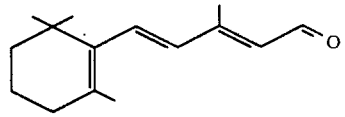

* * * * *